US006712777B1

(12) United States Patent
Kurono et al.

(10) Patent No.: US 6,712,777 B1
(45) Date of Patent: Mar. 30, 2004

(54) EXHIBITED MUSCULAR POWER ESTIMATING APPARATUS

(75) Inventors: Takehiro Kurono, Hamamatsu (JP); Tsunehiko Takeuchi, Hamamatsu (JP); Takahito Kato, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 133 days.

(21) Appl. No.: 10/070,383

(22) PCT Filed: Aug. 30, 2000

(86) PCT No.: PCT/JP00/05878
§ 371 (c)(1),
(2), (4) Date: Mar. 6, 2002

(87) PCT Pub. No.: WO01/17430
PCT Pub. Date: Mar. 15, 2001

(30) Foreign Application Priority Data

Sep. 6, 1999 (JP) .......................... P11-251584

(51) Int. Cl.[7] .................................................. A61B 5/22
(52) U.S. Cl. ..................................................... 600/587
(58) Field of Search ............................... 600/323, 333, 600/587, 595; 482/1, 8; 73/379.01

(56) References Cited

FOREIGN PATENT DOCUMENTS

| JP | 6-38948 | 2/1994 |
|----|---------|--------|
| JP | 6-142086 | 5/1994 |

OTHER PUBLICATIONS

McCully, K.K. et al., "Noninvasive Measurements of Activity–Induced Changes in Muscle Metabolism," Journal of Biomechanics, vol. 24, Suppl. 1, pp. 153–161, 1991.*

Belardinelli, R. et al. "Changes in Skeletal Muscle Oxygenation During Incremental Exercise Measured with Near Infrared Spectroscopy," European Journal of Applied Physiology and Occupational Physiology, vol. 70, No. 6, pp. 487–492, 1995.*

Boushel R. et al., "Muscle Metabolism from Near Infrared Spectroscopy During Rhythmic Handgrip in Humans," European Journal of Applied Physiology, vol. 79, No. 1, pp. 41–48, 1998.*

* cited by examiner

Primary Examiner—Eric F. Winakur
(74) Attorney, Agent, or Firm—Morgan, Lewis & Bockius LLP

(57) ABSTRACT

A muscular strength estimation device according to the present invention comprises load supply means 1 for applying a prescribed exercise load to a subject; oxygen saturation measuring means 2 for measuring, while the exercise load is being applied to the subject, the oxygen saturation in the blood circulating through the muscle to which the exercise load is applied; minimum value detection means 3 for detecting the oxygen saturation minimum value during measurement; recording means 5 for recording in advance a correlation table showing the correlation between the subject's oxygen saturation and muscular strength; and calculation means 6 for calculating the muscular strength corresponding to the oxygen saturation minimum value, from the correlation table.

2 Claims, 4 Drawing Sheets

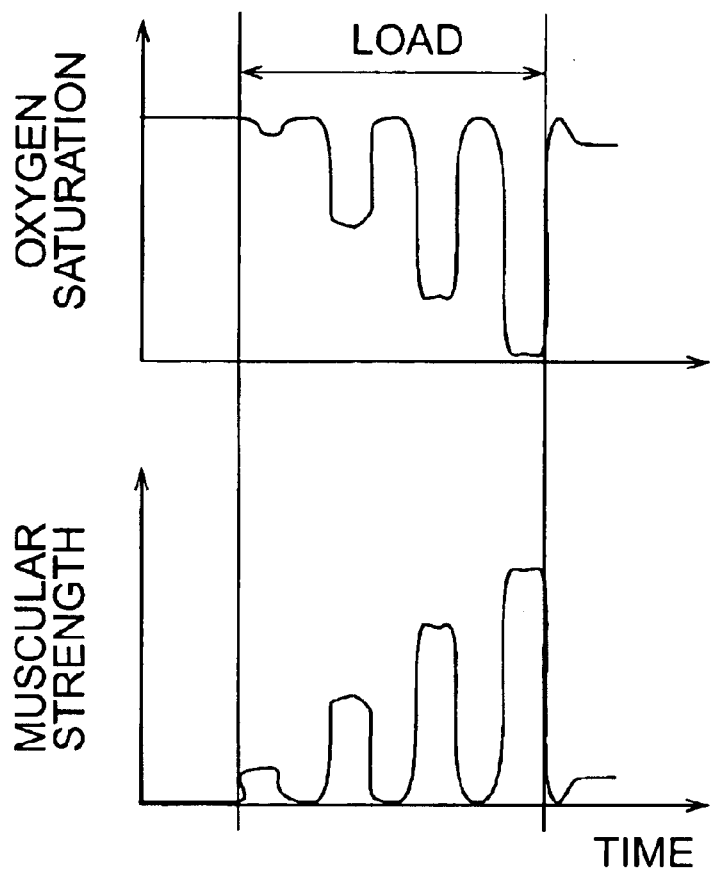
Fig.1A
Fig.1B
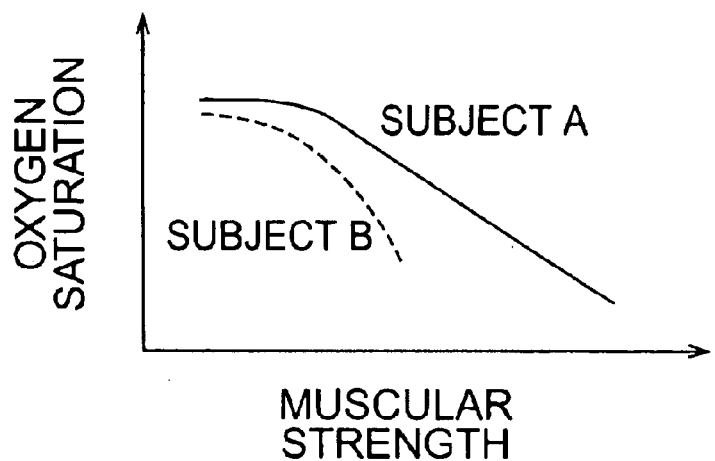
Fig.2 exercise intensity, at the sane time affecting $HbO_2$ and $Hb$. Therefore it is impossible to accurately monitor the change in oxygen concentration with these parameters. On the other hand, $SO_2$ (oxygen saturation) is not affected by a change in exercise intensity, and since it changes in response to the degree of muscular exercise, by detecting oxygen saturation it is possible to estimate the force exerted by the muscles.

EXHIBITED MUSCULAR POWER ESTIMATING APPARATUS

TECHNICAL FIELD

The present invention relates to a device that is able to evaluate the exercise capacity and exercise fitness of a living organism. More particularly, it relates to a muscular strength estimation device that is able to estimate muscular strength by measuring oxygen saturation or the like with simple means using non-invasive optical technology.

BACKGROUND ART

Methods that have been used to evaluate muscular exercise capacity and exercise fitness have included invasive methods such as removing muscular tissue, blood analysis by inserting a catheter, and measuring the amount of lactic acid in a small amount of blood obtained by pricking the subject's finger with a needle. However, in recent years it has become possible to use optical technology to measure muscular exercise capacity and exercise fitness non-invasively in real-time with a device that measures the oxygen concentration in the blood circulating through the muscles.

In Japanese Patent Application Laid-open No.H6-142086 an exercise monitoring device is disclosed which uses optical technology to measure the change in the oxygen concentration in the blood circulating through the muscles and determines the subject's maximum exercise tolerance and oxygen uptake. This exercise monitoring device detects the point of inflection in the oxygen concentration in the blood based on the change in the oxygen concentration while the subject is exercising, and determines the subject's maximum exercise tolerance and maximum oxygen uptake based on the exercise tolerance level reached by the subject at the point of inflection.

DISCLOSURE OF THE INVENTION

However, no device yet exists that uses optical technology to measure muscular strength. The force that muscles actually exert is not the same as that which we subjectively perceive and differs from the force that we estimate sensorily. Previously therefore, conducting physical training while estimating muscular capacity scientifically and with certainty imposed a heavy burden on the subject, since major, invasive devices had to be used. This has led to an increase in demand for the development of a device that makes it possible to conduct training non-invasively and scientifically, and devices that use optical technology have begun to attract attention.

One way to estimate the force exerted by muscles using optical technology is to measure the oxygen concentration in the blood circulating through the muscles. Parameters that represent the oxygen concentration in the blood include $HbO_2$, $Hb$, $t-Hb$, and $SO_2$, but $t-Hb$ changes according to exercise intensity, at the sane time affecting $HbO_2$ and $Hb$. Therefore it is impossible to accurately monitor the change in oxygen concentration with these parameters. On the other hand, $SO_2$ (oxygen saturation) is not affected by a change in exercise intensity, and since it changes in response to the degree of muscular exercise, by detecting oxygen saturation it is possible to estimate the force exerted by the muscles.

Therefore, an object of the present invention is to provide a muscular strength estimation device that non-invasively detects oxygen saturation ($SO_2$) in the blood circulating through the muscles using optical technology, making it possible to conduct scientific training while matching subjective perception with muscular strength.

In order to solve the above-mentioned problems, a muscular strength estimation device according to the present invention is a device for estimating muscular strength, comprising: load supply means for applying a prescribed exercise load to a subject; oxygen saturation measuring means for measuring, while the exercise load is being applied to the subject, oxygen saturation in the blood circulating through the muscle to which the exercise load is applied; minimum value detection means for detecting the oxygen saturation minimum value during measurement; recording means for recording in advance a correlation table showing the correlation between the subject's oxygen saturation and muscular strength; and calculation means for calculating the muscular strength corresponding to the oxygen saturation minimum value, from the correlation table. According to the present invention, it is possible to estimate a subject's muscular strength in real-time by a non-invasive method using a simple device.

In addition, a muscular strength estimation device according to the present invention is a device for measuring muscular strength, comprising: load supply means for applying a prescribed exercise load to a subject; oxygen saturation measuring means for measuring, while the exercise load is being applied to the subject, the oxygen saturation in the blood circulating through the muscle to which the exercise load is applied; minimum value detection means for detecting the oxygen saturation minimum value during measurement; recording means for recording in advance the minimum oxygen saturation when the subject was exerting maximum muscular strength; and calculation means for calculating the muscular strength when a prescribed exercise load is applied to the subject, using the subject's oxygen saturation before the exercise load is applied to the subject, the oxygen saturation minimum value that was detected and the minimum oxygen saturation when the subject exerted maximum muscular strength. According to the present invention, it is thus possible to calculate the subject's muscular strength even without correlation table between oxygen saturation and muscular strength.

BRIEF DESCRIPTION OF THE DRAWINGS

FIG. 1A shows the relationship between oxygen saturation and time when a load is applied to the subject interspersed with rest periods;

FIG. 1B shows the relationship between muscular strength and time when a load is applied to the subject interspersed with rest periods;

FIG. 2 shows a correlation table between oxygen saturation and muscular strength;

BEST MODES FOR CARRYING OUT THE INVENTION

Figure 3:
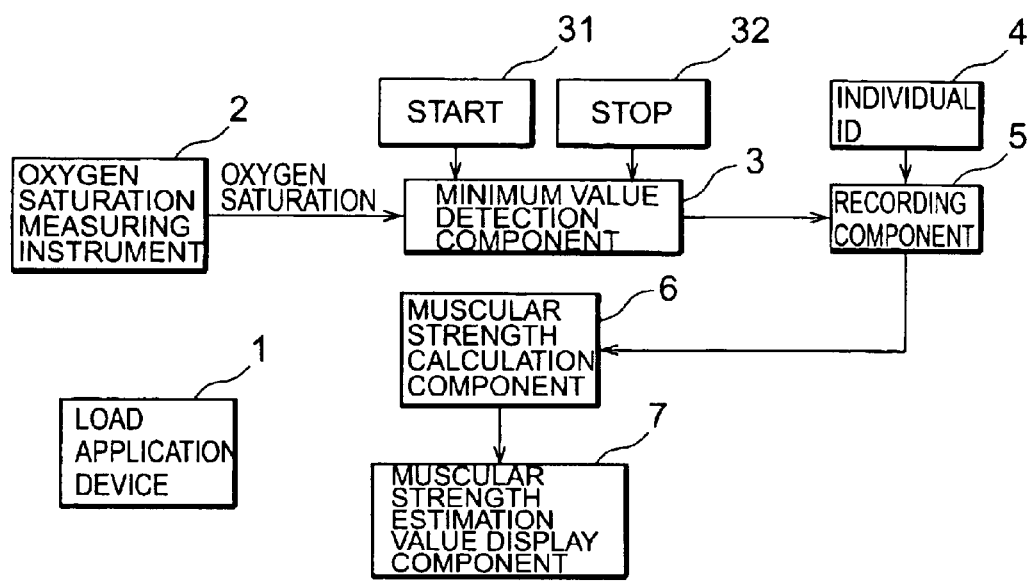
FIG. 3 is a schematic view showing a muscular strength estimation device according to a first embodiment of the present invention.

The first and second embodiments of the present invention will be described below with reference to the accompanying drawings. Note that the same reference numerals are used to refer to the same elements and repeated explanations are omitted.

Before describing the first embodiment, the correlation between oxygen saturation and muscular strength will be described. FIG. 1A and FIG. 1B are graphs showing changes in oxygen saturation over time when loads of 5 Nm, 10 Nm, 20Nm and 30 Nm are applied to the subject in stages, interspersed with rest periods (FIG. 1A), and changes in muscular strength over time calculated using values obtained by means of a dynamometer. From these results it is evident that muscular strength is approximately proportional to oxygen saturation.

Using the measurements in FIG. 1A and FIG. 1B a graph can be drawn as in FIG. 2 showing the relationship between oxygen saturation and muscular strength. As shown in FIG. 2, as muscular strength increases oxygen saturation decreases, and it can be confirmed that when muscular strength reaches a certain threshold, the relationship between oxygen saturation and muscular strength becomes approximately proportional. This graph will be called the oxygen saturation—muscular strength correlation table. Since the slope of this correlation table will change according to a subject's exercise capacity and muscular strength, a correlation table can be constructed for each subject. If such a correlation table is used, the muscular strength that the subject is exerting can be determined from the oxygen saturation measured from the subject.

In addition, the correlation can be determined between the parameters $HbO_2$ and Hb, which represent oxygen concentration in the blood, and muscular strength by correcting for the variation of t-Hb due to exercise intensity, and then constructing a correlation table. Then the muscular strength that the subject is exerting can be determined from the $HbO_2$ and Hb measurements.

Next, the first embodiment of the present invention will be described with reference to FIG. 3. FIG. 3 is a schematic view showing the first embodiment of a muscular strength estimation device that uses a correlation table. The muscular strength estimation device comprises: a load application device 1 to apply an exercise load to a subject; an oxygen saturation measuring instrument 2 to measure oxygen saturation; a minimum value detection component 3 to detect the oxygen saturation minimum value $SO_2$ during measurement; a start switch 31 to indicate the timing of the beginning of the detection; a stop switch 32 to indicate the timing of the end of the detection; an individual ID 4 in which individual parameters are entered such as the subject's build, sex, and oxygen saturation—muscular strength correlation table; a recording component 5 to record the individual parameters stored in the individual ID 4; a muscular strength calculation component 6 to calculate muscular strength using the oxygen saturation $SO_2$ detected by the minimum value detection component 3 together with the subject's oxygen saturation—muscular strength correlation table; and a muscular strength estimation value display component 7 to display the muscular strength as calculated by the muscular strength calculation component 6.

The operation of the muscular strength estimation device as shown in FIG. 3 will now be described. It will be assumed that the contents of the individual ID 4 are already recorded in the recording component 5. First, the size of the load to be applied to the subject is decided and the load application device 1 is set to apply the prescribed load. Next, the light source of the oxygen saturation measuring instrument 2 that uses near-infrared rays, and the probe of the detector (not shown in the drawing), are attached to the muscle that is to be measured (in this embodiment, the biceps muscle of an arm) at an appropriate distance for the light to pass through (in this embodiment, 3 cm) After that, the oxygen saturation measuring instrument 2 is put into operation and the start switch 31 of the minimum value detection component 3 is turned to ON. Next, the prescribed load is applied to the subject's biceps muscle by the load application device 1. Here, the load application device 1 applies a prescribed isometric load to the subject's biceps muscle More specifically, the subject is made to exert the force of the biceps muscle in such a manner as to pull a fixed, unmoving rod towards him or her.

After a prescribed amount of time, the load that was applied to the subject is removed. After that, the oxygen saturation measuring instrument 2 completes measurement and the stop switch of the minimum value detection component 3 is turned to ON. At this time the oxygen saturation minimum value $SO_2$ detected by the minimum value detection component 3 is stored in the recording component 5. Next, the oxygen saturation minimum value $SO_2$ stored in the recording component 5 and the subject's correlation table are sent to the muscular strength calculation component 6. In the muscular strength calculation component 6, the muscular strength corresponding to the oxygen saturation minimum value $SO_2$ that was detected is determined from the correlation table and the muscular strength is displayed in the muscular strength estimation value display component 7. In this way, according to this embodiment, the muscular strength of the subject, when a prescribed load is applied, can be determined. However, because the correlation table changes as the subject's exercise capacity changes, in order to estimate muscular strength more accurately it is necessary to keep remeasuring the correlation table as required.

The first embodiment has been described above, but the present invention is not limited to this. The structure of the muscular strength estimation device is not limited to that which is shown in FIG. 3. For example, if the subject's correlation table is put into graph form as in FIG. 2, the muscular strength corresponding to the measured oxygen saturation of the subject can be confirmed from the correlation table by an observer or the subject him or herself. Further, in FIG. 3, the load is applied for a prescribed time and muscular strength is estimated based on the oxygen saturation minimum value $SO_2$ during that time, but oxygen saturation can be measured in real-time without setting a prescribed period of time. By using the $SO_2$ value at any point in time, muscular strength corresponding to the oxygen saturation $SO_2$ existing at that point in time can be calculated from the correlation table and be displayed and observed on the muscular strength estimation value display component 7 in real-time.

Next, before describing the second embodiment, the relationship between maximum muscular strength and minimum oxygen saturation will be explained. When the subject exerts maximum muscular strength, as can be inferred from FIG. 2, oxygen saturation is at its minimum value $SO_2$min.

Figures 4A, 4B:
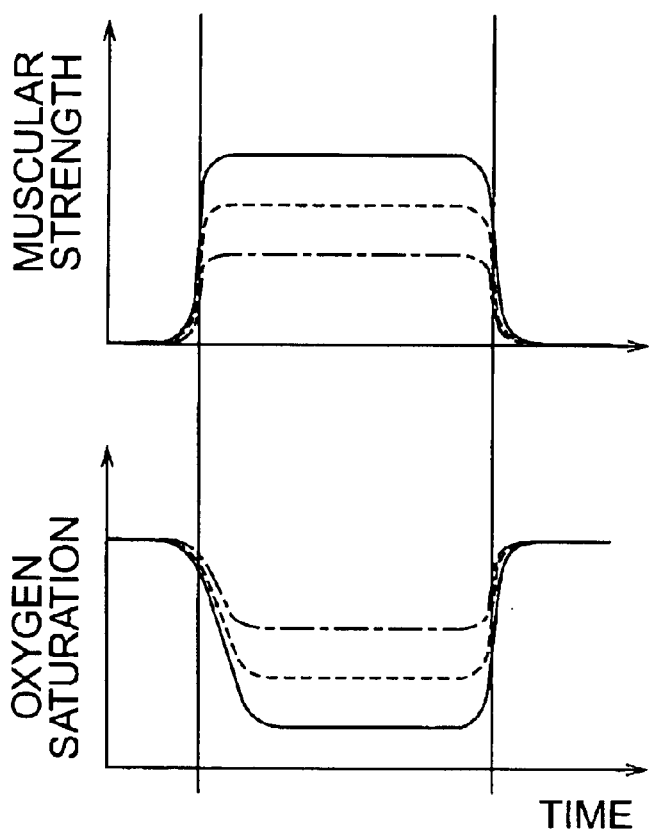
FIG. 4A shows the relationship between maximum muscular strength and time for each subject.
FIG. 4B shows the relationship between oxygen saturation and time when each subject is exerting maximum muscular strength.

The minimum oxygen saturation $SO_2$min can be determined by measuring the oxygen saturation using an oxygen saturation measuring instrument when the subject is exerting maximum muscular strength (as determined by a dynamometer or similar instrument). Maximum muscular strength is different for each subject, however graphs of changes in muscular strength over time and changes in oxygen saturation over time for different subjects exerting their maximum muscular strength are shown in FIG. 4A and FIG. 4B respectively. In this way it can be seen that maximum muscular strength and minimum oxygen saturation $SO_2$min change according to the subject's exercise capacity and muscular strength, Further, as described above, when muscular strength reaches a certain threshold, the relationship between oxygen saturation and muscular strength becomes approximately proportional. Using this proportional relationship and the minimum oxygen saturation $SO_2$min, it is possible to estimate muscular strength without using the oxygen saturation—muscular strength correlation table shown in FIG. 2.

Figure 5:
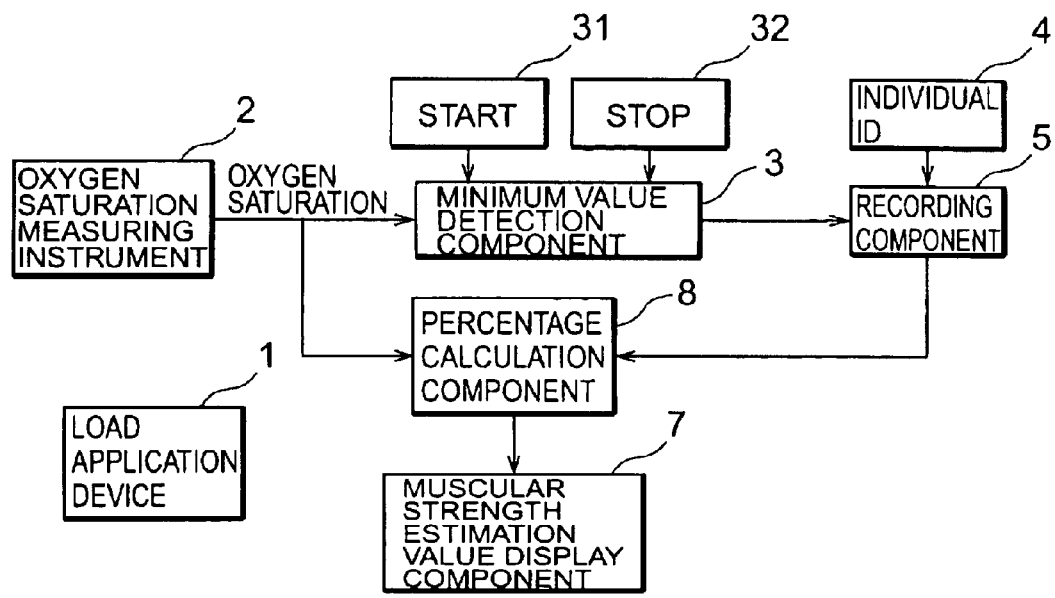
FIG. 5 is a schematic view showing a muscular strength estimation device according to a second embodiment of the present invention.

Next, the second embodiment of the present invention will be described, with reference to FIG. 5. FIG. 5 is a schematic view of the second embodiment of a muscular strength estimation device that uses the proportional relationship between muscular strength and oxygen saturation, and the minimum oxygen saturation $SO_2$min. The muscular strength estimation device comprises: a load application device 1 to apply an exercise load to a subject; an oxygen saturation measuring instrument 2 to measure oxygen saturation; a minimum value detection component 3 to detect the oxygen saturation minimum value $SO_2$ during measurement; a start switch 31 to indicate the timing of the beginning of the detection, and a stop switch 32 to indicate the timing of the end of the detection; an individual ID 4 in which individual parameters are entered such as the subject's build, sex, and minimum oxygen saturation $SO_2$min; a recording component 5 to record the individual parameters stored in the individual ID 4; a percentage calculation component 8 to calculate the muscular strength percentage using the oxygen saturation before the load is applied to the subject $SO_2$pre, the oxygen saturation detected by the minimum value detection component 3 $SO_2$, and the minimum oxygen saturation $SO_2$min; and a muscular strength estimation value display component 7 to display the muscular strength percentage calculated by the percentage calculation component 8.

The operation of the muscular strength estimation device in FIG. 5 will now be described. It will be assumed that the contents of the individual ID 4 are already recorded in the recording component 5. First, the size of the load to be applied to the subject is decided and the load application device 1 is set to apply the prescribed load. Next, the light source of the oxygen saturation measuring instrument 2 that uses near-infrared rays, and the probe of the detector (not shown in the drawing), are attached to the muscle that is to be measured (in this embodiment, the biceps muscle of an arm) at an appropriate distance for the light to pass through (in this embodiment, 3 cm). After that, the oxygen saturation measuring instrument 2 is put into operation and transmits the oxygen saturation $SO_2$pre, which is the value before the prescribed load is applied, to the percentage calculation component 8. Then the start switch 31 of the minimum value detection component 3 is turned to ON. Next, the prescribed load is applied to the subject's biceps muscle by the load application device 1. As described above, here the load application device 1 applies a prescribed isometric load to the subject's biceps muscle. More specifically, the subject is made to exert the force of the biceps muscle in such a manner as to pull a fixed, unmoving rod towards him or her.

After a prescribed amount of time, the load that was applied to the subject is removed. After that, the oxygen saturation measuring instrument 2 completes measurement and the stop switch of the minimum value detection component 3 is turned to ON. At this time the oxygen saturation minimum value $SO_2$ detected by the minimum value detection component 3 is recorded in the recording component 5.

Next, the oxygen saturation minimum value $SO_2$ and the subject's minimum oxygen saturation $SO_2$min are sent to the percentage calculation component 8. At this stage, three parameters will have been sent to the percentage calculation component 8: the oxygen saturation before application of the load ($SO_2$pre), the minimum oxygen saturation when the subject was exerting maximum muscular strength ($SO_2$min), and the oxygen saturation minimum value that was detected ($SO_2$).

Next, the calculation of muscular strength is carried out in the percentage calculation component 8. As described previously, the three parameters used are $SO_2$pre, $SO_2$min and $SO2$, and since oxygen saturation and muscular strength are proportional, the muscular strength percentage is calculated by applying the following formula to the three parameters: Muscular strength $(\%)=(SO_2pre-SO_2)/(SO_2pre-SO_2min)\times 100$ The muscular strength percentage is calculated by this formula and is then sent to the muscular strength estimation value display component 7 where it is displayed. In this way, according to this embodiment it is possible to estimate the muscular strength percentage without an oxygen saturation—muscular strength correlation table. However, this embodiment is only designed to produce an estimate of muscular strength, and it is preferable to use the aforementioned device in FIG. 3 to determine muscular strength more accurately.

The second embodiment has been described above, but the present invention is not limited to this. For example, in FIG. 5, the load is applied for a prescribed time and muscular strength is estimated based on the oxygen saturation minimum value $SO_2$ achieved during that time, but oxygen saturation can be measured in real-time without setting a prescribed period of time. Using this as the $SO_2$ value, by conducting the above-mentioned calculation in the percentage calculation component, muscular strength can be displayed and observed in the muscular strength estimation value display component 7 in real-time. Further, once the maximum muscular strength value for the minimum oxygen saturation $SO_2$min is known, by multiplying this value by the muscular strength percentage estimated, one can calculate the absolute degree of muscular strength exerted similarly to the device in FIG. 3, rather than displaying this value as a percentage.

INDUSTRIAL APPLICABILITY

As described in detail above, a muscular strength estimation device according to the present invention is able to estimate in real-time by a method using optical technology, a subject's muscular strength when a prescribed load is applied, by using an oxygen saturation—muscular strength correlation table. Use of this enables scientific exercise training to be conducted by means of non-invasive method and simple device.

In addition, using the fact that oxygen saturation and muscular strength are proportional to each other, by measuring in advance a subject's minimum oxygen saturation $SO_2$min when he or she is exerting maximum muscular strength, it is possible to estimate the muscular strength percentage without an oxygen saturation—muscular strength correlation table. Therefore, it is not required to prepare in advance a correlation table, which takes time to measure, and by measuring the minimum oxygen saturation $SO_2$min at the time that maximum muscular strength is exerted, the subject is immediately able to begin scientific exercise training.

What is claimed is:

1. A muscular strength estimation device for estimating muscular strength, comprising:
   load supply means for applying a prescribed exercise load to a subject;
   oxygen saturation measuring means for measuring, while said exercise load is being applied to said subject, oxygen saturation in the blood circulating through the muscle to which said exercise load is applied;
   minimum value detection means for detecting said oxygen saturation minimum value during measurement;
   recording means for recording in advance a correlation table showing the correlation between said subject's oxygen saturation and muscular strength; and
   calculation means for calculating the muscular strength corresponding to said oxygen saturation minimum value, from said correlation table.

2. A muscular strength estimation device for estimating muscular strength, comprising:
   load supply means for applying a prescribed exercise load to a subject;
   oxygen saturation measuring means for measuring, while said exercise load is being applied to said subject, oxygen saturation in the blood circulating through the muscle to which said exercise load is applied;
   minimum value detection means for detecting said oxygen saturation minimum value during measurement;
   recording means for recording in advance the minimum oxygen saturation when said subject was exerting maximum muscular strength; and
   calculation means for calculating muscular strength when said prescribed load is applied, using the oxygen saturation before an exercise load is applied to said subject, said oxygen saturation minimum value that has been detected, and said minimum oxygen saturation recorded by said recording means.

* * * * *